US005708035A

United States Patent [19]
Young et al.

[11] Patent Number: 5,708,035
[45] Date of Patent: Jan. 13, 1998

[54] METHODS OF USE AND COMPOSITIONS OF R(-) FLUOXETINE

[75] Inventors: James W. Young, Palo Alto, Calif.; Timothy J. Barberich, Concord; Martin H. Teicher, Wellesley, both of Mass.

[73] Assignees: Sepracor Inc., Marlborough; McLean Hospital, Belmont, both of Mass.

[21] Appl. No.: 446,348

[22] Filed: May 22, 1995

Related U.S. Application Data

[63] Continuation of Ser. No. 080,374, Jun. 18, 1993, abandoned, which is a continuation-in-part of Ser. No. 650,385, Feb. 4, 1991, abandoned, which is a continuation-in-part of Ser. No. 793,062, Nov. 15, 1991, abandoned, which is a continuation-in-part of Ser. No. 794,264, Nov. 15, 1991, abandoned.

[51] Int. Cl.$^6$ ................................................. A61K 31/35
[52] U.S. Cl. ...................... 514/649; 514/651; 514/654
[58] Field of Search ............................ 514/149, 651, 514/654, 655, 251, 258

[56] References Cited

U.S. PATENT DOCUMENTS

| | | | |
|---|---|---|---|
| 3,536,809 | 10/1970 | Applezweig | 424/28 |
| 3,598,123 | 8/1971 | Zaffaroni | 128/268 |
| 3,630,200 | 12/1971 | Higuchi | 128/260 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,018,895 | 4/1977 | Molloy et al. | 424/330 |
| 4,194,009 | 3/1980 | Molloy et al. | 424/330 |
| 4,313,896 | 2/1982 | Molloy et al. | 260/501.18 |
| 4,314,081 | 2/1982 | Molloy et al. | 564/347 |
| 4,329,356 | 5/1982 | Holland | 424/274 |
| 4,444,778 | 4/1984 | Coughlin | 424/262 |
| 4,590,213 | 5/1986 | Stark | 514/653 |
| 4,594,358 | 6/1986 | Hynes | 514/651 |
| 4,596,807 | 6/1986 | Crosby | 514/277 |
| 4,626,549 | 12/1986 | Molloy et al. | 514/651 |
| 4,647,591 | 3/1987 | Cherkin et al. | 514/651 |
| 4,698,342 | 10/1987 | Crosby | 514/253 |
| 4,777,173 | 10/1988 | Shrotyia et al. | 514/252 |
| 4,797,286 | 1/1989 | Thakkar et al. | 424/456 |
| 4,847,092 | 7/1989 | Thakkar et al. | 424/456 |
| 4,868,344 | 9/1989 | Brown | 568/812 |
| 4,895,845 | 1/1990 | Seed | 514/252 |
| 4,918,207 | 4/1990 | Brown | 549/504 |
| 4,918,242 | 4/1990 | Brown | 568/658 |
| 4,918,246 | 4/1990 | Brown | 568/812 |
| 4,971,998 | 11/1990 | Wurtman et al. | 514/654 |
| 5,356,934 | 10/1994 | Robertson et al. | 514/649 |

FOREIGN PATENT DOCUMENTS

| | | |
|---|---|---|
| 0 294 028 A2 | 12/1988 | European Pat. Off. . |
| 0 369 685 A1 | 5/1990 | European Pat. Off. . |
| 0 449 561 A2 | 10/1991 | European Pat. Off. . |
| 0 449 562 A2 | 10/1991 | European Pat. Off. . |
| WO 89/03692 | 5/1989 | WIPO . |

OTHER PUBLICATIONS

Power-Smith, "Beneficial Sexual Side-effects from Fluoxetine," *Brit. J. Psychiatry* 164:249-250 (1994).

Saper et al., "Double-Blind Trial of Fluoxetine: Chronic Daily Headache and Migraine," *Headache* 34:497-502 (1994).

Stevens et al., "Interaction of the Enantiomers of Fluoxetine and Norfluoxetine with Human Liver Cytochromes P450," *J. Pharmacology & Experimental Therapeutics* 226(7):964-971 (1993).

Bergstrom et al., "Quantification and Mechanism of the Fluoxetine and Tricyclic Antidepressant Interaction," *Clin. Pharmacol. Ther.* 51:239-248 (1992).

Adly et al., "Fluoxetine Prophylaxis of Migraine," *Headache* 32:101-104 (1992).

Caccia et al., "Influence of Dose and Route of Administration on the Kinetics of Fluoxetine and Its Metabolite Norfluoxetine in the Rat", *Psychopharmacology* 100:509-514 (1990).

Physicians Desk Reference, pp. 905-908, 44th Ed., Medical Economics Data Production Co., N.J. (1990).

Teicher et al., "Emergence of Intense Suicidal Preoccupation During Fluoxetine Treatment", *Am. J. Psychiatry* 147(2):207-210 (1990).

Wong et al., "Fluoxetine and Its Two Enantiomers as Selective Serotonin Uptake Inhibitors", *Acta Pharm. Nord.* 2(3):171-180 (1990).

Corey and Reichard, "Enantioselective and Practical Synthesis of R-and S-Fluoxetines", *Tetrahedron Lett.* 30(39):5207-5210 (1989).

Coutts and Baker, "Implications of Chirality and Geometric Isomerism in Some Psychoactive Drugs and Their Metabolites", *Chirality* 1:99-120 (1989).

Coutts and Baker, "Metabolic Implications of Chiral Centres in Psychotropic Drugs", *Prog. Neuro-Psychopharmacol. & Biol. Psychiat.* 13:405-417 (1989).

Jamali et al., "Enantioselective Aspects of Drug Action and Disposition: Therapeutic Pitfalls", *J. Pharm. Sci.* 78(9):695-715 (1989).

Gao and Sharpless, "Asymmetric Synthesis of Both Enantiomers of Tomoxetine and Fluoxetine. Selective Reduction of 2,3-Epoxycinnamyl Alcohol with Red-Al", *J. Org. Chem.* 53(17):4081-4084 (1988).

Kim and Wurtman, "Selective Effects of CGS 10686B, dl-Fenfluramine or Fluoxetine on Nutrient Selection", *Physiology & Behavior* 42:319-322 (1988).

(List continued on next page.)

*Primary Examiner*—Theodore J. Criares
*Attorney, Agent, or Firm*—Pennie & Edmonds LLP

[57] ABSTRACT

A method and composition are disclosed utilizing the pure R(-) isomer of fluoxetine which is a potent antidepressant and appetite suppressant substantially free of adverse effects. In addition, a method and composition are disclosed utilizing the pure R(-) isomer of fluoxetine which is useful to treat migraine headaches, pain, in particular chronic pain, psychoactive substance abuse disorders and obsessive compulsive disorders.

20 Claims, No Drawings

OTHER PUBLICATIONS

Robertson et al., "Absolute Configurations and Pharmacological Activities of the Optical Isomers of Fluoxetine, a Selective Serotonin–Uptake Inhibitor", *J. Med. Chem.* 31:1412–1417 (1988).

Wong et al., "Suppression of Food Intake in Rats by Fluoxetine: Comparison of Enantiomers and Effects of Serotonin Antagonists", *Pharmacology Biochemistry & Behavior* 31:475–479 (1988).

Benfield et al., "Fluoxetine: A Review of Its Pharmacodynamic and Pharmacokinetic Properties, and Therapeutic Efficacy in Depressive Illness", *Drugs* 32:481–508 (1986).

Fuller and Snoddy, "Fluoxetine Enantiomers as Antagonists of p–Chloroamphetamine Effects in Rats", *Pharmacology Biochemistry & Behavior* 24:281–284 (1986).

Scrips' New Product Review, No. 7, pp. 13–14 (1986).

Wong et al., "Inhibition of Serotonin Uptake by Optical Isomers of Fluoxetine", *Drug Development Research* 6:397–403 (1985).

Bremner, "Fluoxetine in Depressed Patients: A Comparison with Imipramine", *J. Clin. Psychiatry* 45(10):414–420 (1984).

5,708,035

METHODS OF USE AND COMPOSITIONS OF R(-) FLUOXETINE

This is a continuation of application Ser. No. 08/080,374, filed Jun. 18, 1993 now abandoned; which is a continuation-in-part of application Ser. No. 07/650,385 filed Feb. 18, 1993, now abandoned; which is a continuation-in-part of Ser. No. 07/793,062 filed Nov. 15, 1991, now abandoned; which is a continuation-in-part application of Ser. No. 07/794,264, filed Nov. 15, 1991, now abandoned.

1. BACKGROUND OF THE INVENTION

This invention relates to a novel composition of matter containing optically pure R(-) fluoxetine. This composition possesses potent antidepressant and appetite suppressant activity as a serotonin uptake inhibitor while avoiding the usual adverse effects associated with the racemic mixture of fluoxetine. Furthermore, this composition possesses potent activity as a serotonin uptake inhibitor which can be utilized in the treatment of migraine headaches, pain, psychoactive substance use disorders, and obsessive compulsive disorders, while avoiding the usual adverse effects associated with the racemic mixture of fluoxetine. Also disclosed are methods to treat depression, migraine headaches, pain, obsessive compulsive disorders, and psychoactive substance use disorders, and to effect appetite suppression in a human by administering pure R(-) fluoxetine. This also avoids the usual adverse effects associated with the racemic mixture of fluoxetine.

The active compound of this composition and method is an optical isomer of the compound fluoxetine which is described in U.S. Pat. Nos. 4,018,895 and 4,194,009 to Molloy, et al. Chemically, the R(-) isomer is (-)N-methyl-3-phenyl-3-[($\alpha,\alpha,\alpha$-trifluoro-p-tolyl)-oxy]-propylamine, herein after referred to as R(-) fluoxetine.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (-) or d and l are employed to designate the sign of rotation of plane-polarized light by the compound, with (-) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of propranolol, which is known to be 100 times more potent than the D-enantiomer.

Furthermore, optical purity is important since certain isomers may actually be deleterious rather than simply inert. For example, it has been suggested that the D-enantiomer of thalidomide is a safe and effective sedative when prescribed for the control of morning sickness during pregnancy and that the corresponding L-enantiomer is a potent teratogen.

Fluoxetine's primary use is in the treatment of depression, which along with mania falls under the heading of affective disorders. Mania and depression are characterized by changes in mood as the primary symptom.

Depression is characterized by feelings of intense sadness or pessimistic worry, agitation, self-deprecation, neurovegetative changes and symptoms such as insomnia, anorexia, and loss of drive, enthusiasm, and libido, and mental slowing. Among the more common treatments for depression are the administration of a tricyclic antidepressant agent.

Fluoxetine is not chemically related to any other typical antidepressive agent including tricyclic antidepressants. The antidepressant action of fluoxetine is presumed to be based on its highly specific inhibition of serotonin uptake at serotonergic reuptake sites in the brain.

Fluoxetine can also be used to assist in weight loss as disclosed in U.S. Pat. No. 4,895,845 to Seed. The causes of excess body weight and/or obesity are complex, however a common denominator in the overweight person's diet is a caloric intake which exceeds that person's body expenditures. Fluoxetine is unique as an agent for weight loss since it appears to modify the compulsion to eat in an overweight individual.

It has also been suggested that fluoxetine could be used to treat migraine headaches which are a paroxysmal disorder characterized by recurrent attacks of said headache, with or without associated visual and gastrointestinal disturbances. The cause is unknown, but evidence suggests a genetically transmitted functional disturbance of cranial circulation. Prodromal symptoms may be due to intracerebral vasoconstriction, and the head pain to dilation of scalp arteries. Migraine may occur at any age but usually beings between ages 10 and 30, more often in women than in men. Migraine headaches may be preceded by a short period of depression, irritability, restlessness or anorexia, and in some patients by scintillating scotomas, visual field defects, paresthesias, or (rarely) hemiparesis. These symptoms may disappear shortly before the headache appears or may merge with it. Pain is either unilateral or generalized. Symptoms usually follow a pattern in each patient, except that unilateral headaches may not always be on the same side. The patient may have attacks daily or only once in several months.

In addition, it has been suggested that fluoxetine could be used to treat pain, in particular chronic pain. Pain is a complex subjective phenomenon comprised of a sensation indicating real or potential tissue damage and the affective response this generates. Pain can be classified as either acute or chronic pain. Acute pain is an essential biologic signal of the potential for or the extent of injury. It is usually short-lived and is associated with hyperactivity of the sympathetic nervous system; eg, tachycardia, increased respiratory rate and blood pressure, diaphoresis, and pupillary dilation. The concurrent affect is anxiety. Treatment involves removal of the underlying etiology if possible and the use of analgesic drugs.

Chronic pain is defined as pain persisting for greater than six months. Pain of this duration loses its adaptive biologic role. Vegetative signs gradually develop; eg, lassitude, sleep disturbance, decreased appetite, loss of taste for food, weight loss, diminished libido, and constipation. A depressed affect predominates. In many patients, organic disease may be insufficient to explain the degree of pain or may be altogether absent. In these patients, as well as in many with organic disease, the psychologic factors become the primary contributor to impairment. Therapy is often difficult and prognosis is guarded.

It also has been postulated that fluoxetine is effective in the treatment of obsessive-compulsive disorders. This is a neurotic disorder characterized by the presence of recurrent ideas and fantasies (obsessions) and repetitive impulses or actions (compulsions) that the patient recognizes as morbid and toward which he feels a strong inner resistance. Anxiety is a central feature, but in contrast to the phobias (where the patient is anxious in the face of external dangers of which he perceives himself to be the passive victim), the anxiety arises in response to internally derived thoughts and urges that the patient fears he may actively carry out despite his wishes not to. Obsessive-compulsive patients comprise less than 5% of those with neurotic disorders, and about 0.05% of the population at large. The neurosis affects men and women equally and tends to be found in individuals from upper socioeconomic levels and with higher intelligence.

Furthermore, it has been suggested that fluoxetine is effective in the treatment of psychoactive substance use disorders. These disorders encompass, but are not limited to, abuse and/or dependence on alcohol, cocaine, nicotine, caffeine, and opiates (e.g. heroin, morphine) whereby drug-seeking behavior takes up a large proportion of the individual's time and resources, and results in inappropriate behavior. Psychoactive substance use disorders occur in more than 20 million people in the United States alone, and are among the most difficult conditions to treat. Fluoxetine may reduce craving, improve symptoms of depression, and result in an improved treatment outcome.

At the present time, fluoxetine is available only as a racemic mixture. That is, it is a mixture of optical isomers, called enantiomers.

The racemic mixture of fluoxetine, in addition to its use as an antidepressant and appetite suppressant, has been shown to have a wide spectrum of action which includes:

Treatment of diabetes (EPA 88303930.7)

Treatment of alcohol abuse (U.S. Pat. No. 4,777,173)

Analgesia—control of pain (U.S. Pat. Nos. 4,698,342 and 4,594,358)

Treatment of atherosclerosis (U.S. Pat. No. 4,444,778)

Improvement of memory (U.S. Pat. No. 4,647,591)

Treatment of anxiety (U.S. Pat. No. 4,590,213)

Treatment of hypertension (U.S. Pat. No. 4,329,356)

Whereas the foregoing Molloy et al. patents, in addition to the above discussed European patent application and U.S. patents, recognize compounds such as fluoxetine have optically active forms, no example of an optically active form is given. Furthermore, certain studies with the-enantiomers of fluoxetine have generally concluded that there is no advantage in the use of the pure R(−)enantiomer. See, Robertson et al., *J. Med. Chem.*, 31: pg. 1412–1417 (1988).

Various researchers have presented a limited amount of pharmacological data on the enantiomers of fluoxetine. See, Fuller et al., *Pharm. Biochem. Behav.*, 24: pg. 281–284 (1986); Robertson et al., *J. Med. Chem.*, 31: pg. 1412–1417 (1988); Wong et al. *Drug Devel. Res.* 6: pg. 397–403 (1985); Wong et al., *Pharm. Biochem. Behav.*, 31: pg. 475–479 (1988). These references are limited by their failure to provide complete dose-response or pharmacokinetic analyses, resulting only in qualitative impressions on certain matters. The results of the above described studies are summarized in Table I below.

|  | RS (±) | R (−) | S (+) | dose | ref |
|---|---|---|---|---|---|
| 5HT uptake cortical synaptasomes ($K_i$) | 30 | 33 | 21 | nM | 1 |
| 5HT uptake cortical synaptasomes ($IC_{50}$) |  | 99.5 | 61.5 | nM | 2 |
| Inhibition of 3H-fluoxetine | 5.7 | 7.7 | 4.1 | nM | 1 |

-continued

|  | RS (±) | R (−) | S (+) | dose | ref |
|---|---|---|---|---|---|
| binding ($IC_{50}$) |  |  |  |  |  |
| Inhibition of 5HT uptake Ex Vivo brainstem ($ED_{50}$) | 9.3 | 8.7 | 7.4 | mg/kg | 1 |
| Inhibition of PCPA effect on 5HT (full block) |  | ~10 | ~5 | mg/kg | 3 |
| Inhibition of PCPA effect on 5HT ($ED_{50}$) |  | 2.1 | 1.2 | mg/kg | 4 |
| Inhibition of Feeding (meal fed, 2DG) (rel. potency) |  | R < | S |  | 2 |
| Inhibition of Saccharine palatability ($ED_{50}$) |  | 6.1 | 4.9 | mg/kg | 4 |
| Inhibition of acetic acid writhing ($ED_{50}$) |  | 15.3 | 25.7 | mg/kg | 4 |
| Inhibition of writhing (morphine potentiation; $ED_{50}$) |  | 3.6 | 5.7 | mg/kg | 4 |
| Duration of 5HT uptake inhibition Ex Vivo |  | ~8 hr | >24 hr |  | 1 |
| Duration of Inhibition of PCPA 5HT effect |  | ~8 hr | >24 hr |  | 3 |

[1] Wong et al 1985
[2] Wong et al 1988
[3] Fuller & Snoddy 1986
[4] Robertson et al 1988

Briefly, the first part of the table indicates that the S(+) enantiomer is about 1.5 fold more potent in antagonizing 5HT uptake, and is probably slightly more potent in suppressing food intake. The second part of the table suggests that the R(−) enantiomer may be about 1.5 fold more potent in antagonizing pain, or potentiating morphine analgesia. The third part of the table clearly suggests that the S(+) enantiomer has a substantially greater duration of action (approximately 24 hours), than the R(−) isomer, (approximately 8 hours). Additional data published by Wong et al., *Pharm. Biochem. Behav.* 31: pg. 475–479 (1988) suggests that both the S(+) and R(−) forms have relatively little affinity for $5HT_1$, $5HT_{1A}$, $5HT_2$, $\alpha_1$, $\alpha_2$, $\beta$, $D_1$, $D_2$, $H_1$, and $M_1$ receptors, or the uptake of norepinephrine relative to their effect on 5HT uptake.

The racemic mixture of fluoxetine has been shown to have certain advantages over other antidepressant drugs. Antagonism of muscarinic, histaminergic and α1 adrenergic receptors has been hypothesized to be associated with various anticholinergic and cardiovascular effects of classical tricyclic antidepressant drugs. Fluoxetine binds to these and other membrane receptors from brain tissue much less potently than do these tricyclic antidepressants. Thus, fluoxetine gives less anticholinergic side effects such as blurred vision, dry mouth, constipation and urinary retention. There is also less lowering of blood pressure, tachycardia and arrhythmias.

While the racemic mixture of fluoxetine has certain advantages, it also has disadvantages. Among these disadvantages are adverse effects other than the ones described above. The most frequent reported adverse effects associated with fluoxetine are headaches, nervousness, anxiety and insomnia. These are reported by 10% to 15% of patients treated with fluoxetine. These symptoms led to drug discontinuation in 5% of the patients treated with the drug. With regard to insomnia, often patients being treated with fluoxetine must be administered sleep medication such as benzodiazepine hypnotics or sedating antidepressants in the evening to counteract the insomnia. Furthermore, fluoxetine produces a state of inner restlessness (akathisia), which is one of its more significant side effects. In all likelihood this is a result of the effect fluoxetine has on dopamine turnover in the striatum. Baldessarini et al. *Arch. Gen. Psychiatry,*

47(2), pg. 191–192 (1990). It is also known that in some patients, use of fluoxetine is associated with severe anxiety leading to intense violent suicidal thoughts and self mutilation. Teicher et al., *Am. J. Psychiatry,* 147:2 pg. 207–210 (1990). In other patients manic behavior follows treatment with fluoxetine. Other side effects associated with fluoxetine include nausea, diarrhea, drowsiness, decrease in libido, and/or sexual dysfunction.

Another disadvantage of the racemic mixture of fluoxetine is its long half-life and long duration of action. Since the S(+) isomer of fluoxetine has a half life approximately three times that of the R(−) isomer, the long half life of the racemic mixture in all likelihood can be attributed to the amount of the S(+) isomer found in the racemic mixture. This long half life can lead to a buildup of fluoxetine in the patient's body and a concomitant increase in the above described side effects when a patient is given multiple doses.

It is therefore desirable to find a compound with the advantages of fluoxetine which would not have the above described disadvantages.

2. SUMMARY OF THE INVENTION

It has now been discovered that the R(−) isomer of fluoxetine is an effective antidepressant and appetite suppressant, which because of its short half life and short duration of action, will not accumulate in a patient's body, thus decreasing the incidence of adverse effects seen with the racemic mixture of fluoxetine. It has also been discovered that the R(−) isomer of fluoxetine is useful in the treatment of migraine headaches, the treatment of pain, in particular chronic pain, in the treatment of psychoactive substance use disorders and the treatment of obsessive compulsive disorders, for the above-described reasons. The adverse affects which are decreased by administering the R(−) isomer of fluoxetine include but are not limited to headaches, nervousness, anxiety, insomnia, inner restlessness (akathisia) suicidal thoughts and self mutilation. Novel compositions of matter containing optically pure R(−) fluoxetine which have antidepressant and appetite suppressant activity while avoiding the above described adverse effects associated with the racemic mixture of fluoxetine are also disclosed. Also included within the present invention are novel compositions of matter containing optically pure R(−) fluoxetine which are useful in the treatment of migraine headaches, the treatment of pain, in particular chronic pain, the treatment of psychoactive substance use disorders and the treatment of obsessive compulsive disorders. These novel compositions also avoid the above-described adverse effects associated with the racemic mixture of fluoxetine. In addition to its short half life and short duration of action decreasing adverse effects, using the pure R(−) isomer of fluoxetine will also decrease the adverse effects associated with the racemic mixture of fluoxetine.

3. DETAILED DESCRIPTION OF THE INVENTION

The present invention encompasses a method of eliciting an antidepressant effect while avoiding adverse effects which comprises administering to a patient in need of antidepressant therapy an amount sufficient to alleviate human depression but insufficient to cause said adverse effects of R(−) fluoxetine or a pharmaceutically acceptable salt thereof, substantially free of its S(+) stereoisomer.

The present invention further encompasses a method of suppressing the appetite of a patient while avoiding concomitant liability of adverse effects, comprising administering to a patient in need of appetite suppression an amount sufficient to suppress the patient's appetite but insufficient to cause said adverse effects, of R(−) fluoxetine or a pharmaceutically acceptable salt thereof, substantially free of its S(+) stereoisomer.

In addition, the present invention encompasses a method of treating migraine headaches, pain, psychoactive substance use disorders or obsessive compulsive disorders while avoiding concomitant liability of adverse effects, comprising administering to a patient in need of treatment of migraine headaches, treatment of pain, treatment of psychoactive substance use disorders or treatment of obsessive compulsive disorders, an amount sufficient to treat the patient's migraine headache, pain, psychoactive substance use disorders or obsessive compulsive disorders but insufficient to cause said adverse effects, of R(−) fluoxetine or a pharmaceutically acceptable salt thereof, substantially free of its S(+) stereoisomer.

The present invention also encompasses an antidepressant composition adapted for the treatment of a patient in need of antidepressant therapy which comprises an amount sufficient to alleviate human depression but insufficient to cause adverse effects, of R(−) fluoxetine or a pharmaceutically acceptable salt thereof, substantially free of its S(+) stereoisomer.

Also embodied in the present invention is an appetite suppression composition adapted to be administered to a patient in need of appetite suppression, comprising an amount sufficient to suppress the appetite of a patient but insufficient to cause adverse effects, of R(−) fluoxetine or a pharmaceutically acceptable salt thereof, substantially free of its S(+) stereoisomer.

In addition, the present invention encompasses compositions that are adapted for treating migraine headaches, pain, psychoactive substance use disorders or obsessive compulsive disorders, comprising an amount sufficient to alleviate the above-described afflictions, but insufficient to cause adverse effects, of R(−) fluoxetine or a pharmaceutically acceptable salt thereof, substantially free of its S(+) stereoisomer.

Pure R(−) fluoxetine functions as an effective antidepressant with a shorter half life and shorter duration of action than the racemic mixture or the S(+) isomer of fluoxetine. Having a shorter half life and shorter duration of action results in less accumulation of R(−) fluoxetine in a patient's body. This in turn results in decreased adverse effects including headaches, nervousness, anxiety, insomnia, inner restlessness (akathisia), nausea, diarrhea, drowsiness, decreased libido and/or sexual dysfunction, suicidal thoughts and self mutilation. With regard to insomnia, pure R(−) fluoxetine is particularly effective in that it will allow for less interrupted sleep if administered to the patient in the morning. Because of its short half life and short duration of action, R(−) fluoxetine will have less effect at night since by this time a large portion of the compound will have been cleared from the patient's body, thus decreasing the incidence of insomnia. Furthermore, the short half life and short duration of action of R(−) fluoxetine makes it valuable in patients who may require subsequent treatment with monoamine oxidase inhibitors (MAOI). Presently, patients who are taking the racemic mixture of fluoxetine with its long half life and long duration of action, must wait 5–6 weeks after discontinuing fluoxetine before starting treatment with an MAOI.

In addition, pure R(−) fluoxetine is of greater use as an appetite suppressant, since as discussed above the short half life and short duration of action will lead to a decrease in adverse effects. Furthermore, pure R(−) fluoxetine is a more effective appetite suppressant since the racemic mixture and both isomers of fluoxetine effectively suppress the appetite only when given before meals. Because of their long half life and duration of action this would lead to unnecessary accumulation of the racemic mixture or the S(+) isomer of fluoxetine if they are administered in multiple doses. By administering the pure R(−) isomer of fluoxetine, with its shorter half life, this unnecessary accumulation and adverse effects can be avoided.

Furthermore, pure R(−) fluoxetine is also more effective for the treatment of migraine headaches, the treatment of pain, in particular chronic pain, the treatment of psychoactive substance use disorders, and the treatment of obsessive compulsive disorders, since as previously discussed the short half life and short duration of action will lead to a decrease in adverse effects. With regard to migraine headaches in particular, the shorter half-life and short duration of action of the R(−) isomer of fluoxetine allows for treatment of the symptoms on an acute basis and also prophylactically, without the previously described adverse effects or complications.

Another advantage of the present invention is the purity of the R(−) isomer of fluoxetine. Using the pure R(−) isomer of fluoxetine as opposed to the racemic mixture or S(+) isomer, leads to a decrease in side effects also.

As used in the present application, the term "substantially free of the S(+) stereoisomer" means that the composition contains at least 90% by weight of R(−) fluoxetine and 10% by weight or less of S(+) fluoxetine. In the most preferred embodiment the term "substantially free of the S(+) stereoisomer" means that the composition contains at least 99% by weight R(−) fluoxetine and 1% or less of S(+) fluoxetine.

The term "eliciting an antidepressant effect" means relief from the symptoms associated with depression, which include but are not limited to feelings of intense sadness or pessimistic worry, agitation, self-deprecation, neurovegetative changes and symptoms such as insomnia, anorexia, and loss of drive, enthusiasm and libido and mental slowing.

The term "adverse effect" as used in the present application includes but is not limited to headaches, nervousness, anxiety, insomnia, inner restlessness (akathisia), suicidal thoughts, self mutilation, manic behavior, nausea, diarrhea, drowsiness, decreased libido, and/or sexual dysfunction.

The synthesis of the S(+) or R(−) isomer of fluoxetine can be performed by two methods which are as follows:

Method 1

This method is disclosed in Gao, et al. *J. Org. Chem.* Vol. 53, No. 17, pp. 4081–4084 (1988). It involves the use of 1-phenyl-1,3-propanediols, which are key intermediates. The 1-phenyl-1,3-propanediols are prepared from cinnamyl epoxy alcohols by Red-AL reduction. The chiral cinnamyl epoxy alcohols are made by, asymmetric epoxidation of cinnamyl alcohols as disclosed in Gao, et al.

The reaction scheme is as follows:

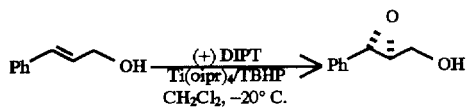

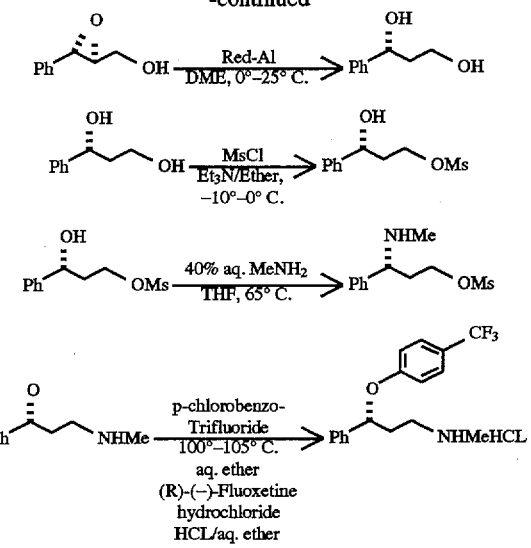

(S)-(+) fluoxetine hydrochloride is prepared from (2R)-Epoxycinnamyl alcohol obtained by the asymmetric epoxidation disclosed in Gao et al. utilizing (−)-DIPT.

Method 2

This method is based on the asymmetric reduction of ketone with a chiral borane reagent as disclosed in U.S. Pat. No. 4,868,344 to H. C. Brown.

The reaction scheme is as follows:

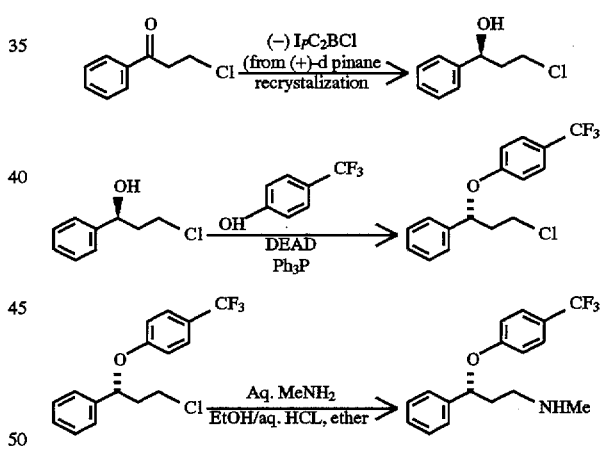

The magnitude of a prophylactic or therapeutic dose of R(−) fluoxetine will, of course, vary with the nature of the severity of the condition to be treated and its route of administration. It will also vary according to the age, weight and response of the individual patient. In general, the daily dose range for use as an anti-depressant or appetite suppressant, and for the treatment of migraine headaches, treatment of pain, in particular chronic pain, treatment of psychoactive substance use disorders and treatment of obsessive compulsive disorders lie within the range of from about 1 mg to about 100 mg per day, preferably about 5 mg to about 60 mg per day, and most preferably from about 10 mg to about 40 mg per day, in single or divided doses. On the other hand, it may be necessary to use dosages outside these limits in some cases. The terms "an amount sufficient to alleviate said human's depression but insufficient to cause said adverse effects" and "an amount sufficient to suppress the appetite of said human but insufficient to cause said adverse effects" are encompassed by the above-described amounts. Furthermore, the term "an amount sufficient to alleviate said human's migraine headaches, pain, psychoactive substance use disorders or obsessive compulsive disorder but insufficient to cause said adverse effects" is encompassed by the above described amounts.

Any suitable route of administration may be employed for providing the patient with an effective dosage of R(−) fluoxetine. For example, oral, rectal, parenteral, transdermal, subcutaneous, intramuscular, inhalation and the like may be employed. Dosage forms include tablets, troches, dispersions, suspensions, solutions, capsules, patches and the like.

The pharmaceutical compositions of the present invention comprise R(−) fluoxetine as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids, including inorganic and organic acids. Such acids include acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred are hydrobromic, hydrochloric, phosphoric and sulfuric acids.

The compositions include compositions suitable for oral, rectal, parenteral (including subcutaneous, intramuscular, and intravenous), although the most suitable route in any given case will depend on the nature and severity of the condition being treated. The most preferred route of the present invention is oral. They may be conveniently presented in unit dosage form and prepared by any of the methods well-known in the art of pharmacy.

In the case where an oral composition is employed, a suitable dosage range for use is, e.g., from about 1 mg to about 100 mg of fluoxetine per day, preferably from about 5 mg to about 60 mg per day and most preferably from about 10 mg to about 40 mg per day.

In practical use, R(−) fluoxetine can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. The most preferred solid oral preparation is capsules. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference. The use of a racemic mixture of fluoxetine in a sustained release formulation is disclosed and/or claimed in U.S. Pat. Nos. 4,797,286 and 4,847,092.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binner, lubricant, inert diluent, surface active or dispersing agent. Molded tablets may be made by molding in a suitable machine, a mixture of the powdered compound moistened with an inert liquid diluent. Desirably, each tablet contains from about 1 mg to about 100 mg of the active ingredient and each cachet or capsule contains from about 1 to about 100 mg of the active ingredient. Most preferably the tablet, cachet or capsule contains about 1 mg to about 60 mg of active ingredient of active ingredient.

The invention is further defined by reference to the following examples describing in detail the preparation of the compound and compositions of the present invention. It will be apparent to those skilled in the art that many modifications, both to materials and methods, may be practiced without departing from the purpose and interest of this invention.

All temperatures are in degrees Celsius.

4. EXAMPLES

4.1 Example 1

Synthesis of R(−) and S(+) Fluoxetine Reduction of epoxycinnamyl alcohols with Red-Al; synthesis of fluoxetine Part 1

(R)-3-Phenyl-1,3-dihydroxypropane

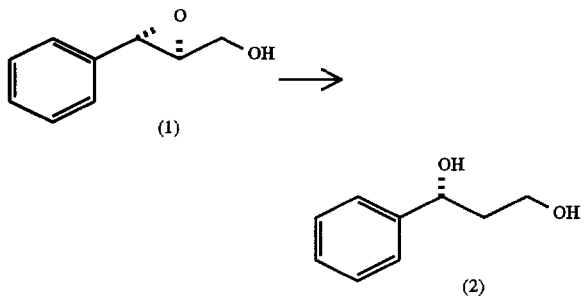

To a solution of (−)-(2S,3S)-epoxycinnamyl alcohol (1) (1.5 g, 10.0 mmol) (synthesized by the method disclosed in Gao et al., *J. Org. Chem.*, Vol. 53, No. 17, pp. 4081–4084 (1988.), in dimethoxyethane (50 mL) was added a 3.4 molar solution of REd-Al in toluene (3.1 mL, 10.5 mmol) dropwise under nitrogen at 0° C. After stirring at room temperature for three hours, the solution was diluted with ether and quenched with 5% HCl solution. After stirring at room temperature for 30 min, the resulting white precipitate formed was filtered and boiled with ethyl acetate and filtered again. The combined organic solutions were dried with magnesium sulfate. Concentration gave (R)-3-phenyl-1,3-dihydroxypropane (2) as a slightly yellow oil which was used without further purification (1.5 g, 98%): $^1$H NMR (CDCl$_3$) δ7.2–7.3 (m, 5 H), 4.88–4.98 (m, 1 H), 3.78–3.86(t, J=7.5 Hz, 2), 3.3–3.4 (br. s, 1 H), 2.85–2.95 (br. s, 1 H), 1.84–2.08 (m, 2 H); the ratio of 1,3-diol to 1,2-diol was 20:1 by $^1$H NMR analysis of the derived diacetate.

(S)-3-Phenyl-1,3-dihydroxypropane (2) was prepared according to the above procedure starting with 300 mg of (+)-epoxycinnamyl alcohol to provide 300 mg of (S)-3-phenyl-1,3-dihydroxypropane (1,3-diol:1,2-diol=21:1).

Part 2

(S)-3-phenyl-3-hydroxypropyl-1-methanesulfonate

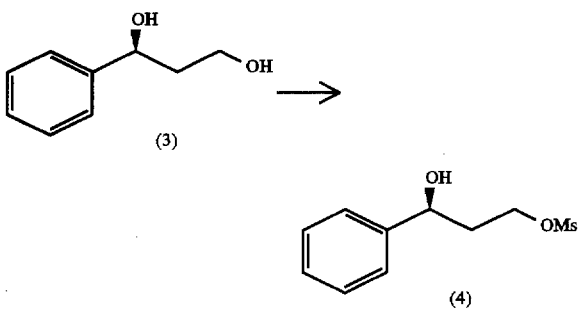

To a solution of (S)-3-phenyl-1,3-dihydroxypropane (3) (2.71 g, 17.8 mmol) and triethylamine (2.60 g, 25.6 mmol) in ether (90 mL) was added dropwise MsCl (1.45 mL, 18.7 mmol) under nitrogen at −10° C. After stirring at −10° C. to 0° C. for 3 h, the mixture was poured into ice water (30 mL) and washed with 20% H$_2$SO$_4$, saturated aqueous NaHCO$_3$, brine, and dried over magnesium sulfate. The crude products were purified by chromatography eluting with 45% ethyl acetate in hexane to give the title compound (4) as an oil (3.50 g, 85%): $^1$H NMR (CDCl$_3$ δ7.3–7.4 (m, 5 H), 4.85–4.91 (t, J=7.7 Hz, 1 H), 4.42–4.52 (m, 1 H), 4.22–4.32 (m, 1 H), 3.0 (s, 3 H), 2.3 (s, 1 H), 2.1–2.2 (q, J=7.7 Hz, 2 H).

(R)-3-Phenyl-3-hydroxypropyl-1-methanesulfonate was prepared from (R)-3-phenyl-1,3-dihydroxypropane by the above procedure in 74% yield.

These two compounds were either stored at 0° C. or used soon after preparation.

Part 3

(S)-N-Methyl-3-phenyl-3-hydroxypropylamine

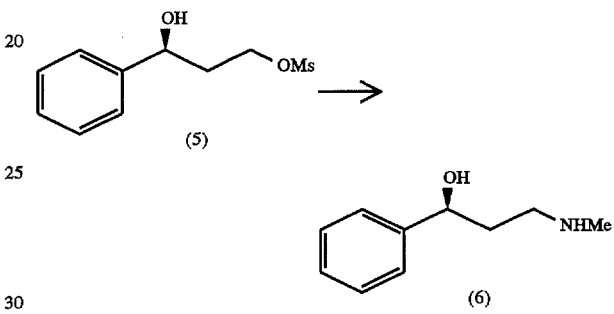

A solution of (S)-3-phenyl-3-hydroxypropyl-1-methanesulfonate (5) (690 mg, 3.0 mmol) and methylamine (10 mL, 40% in water) in THF (10 mL) was heated at 65° C. for 3 h. After cooling, the solution was diluted with ether and washed with saturated aqueous sodium bicarbonate, brine, and dried with anhydrous potassium carbonate. Concentration to dryness provided the title compound (6) (476 mg, 96%): $^1$H NMR (CDCl$_3$) *I704*12*d*I704*10*7.2–7.4 (m, 5 H), 4.94 (dd, J=3.8, 7.2 Hz, 1 H), 3.4–3.9 (br. s, 1 H), 2.84–2.92 (m, 2 H), 2.45 (s, 3 H), 1.68–1.92 (m, 3 H).

Following a procedure identical to the above 1.15 g (R)-3-phenyl-3-hydroxypropyl-1-methanesulfonate yielded 837 mg of (R)-N-methyl-3-phenyl-3-hydroxypropylamine.

Part 4

(R)-Fluoxetine Hydrochloride

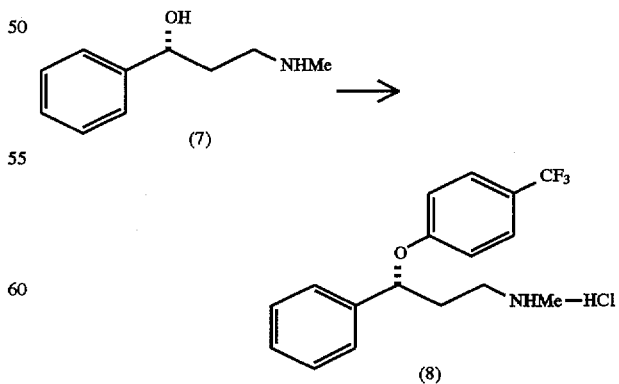

To a solution of (R)-N-methyl-3-phenyl-3-hydroxypropylamine (7) (1.23 g, 7.45 mmol) in dimethyl acetamide (7 mL) was added sodium hydride (215 mg, 8.95 mmol) with cooling. The mixture was heated at 90° C. for 1.5 h, and an orange solution resulted. To this solution was then added 4-chlorobenzotrifluoride (3.23 g, 2.40 mL, 17.9 mmol), and the mixture was heated at 100°–105° C. for 2.5 h. After cooling and dilution with toluene, the mixture was washed with water, and the aqueous layer was separated and extracted with toluene. The combined toluene solutions were then washed with saturated aqueous sodium bicarbonate, brine, and dried over be magnesium sulfate. Concentration provided (R)-fluoxetine as an orange oil (1.97 g, 86%). The oil was dissolved in ether and acidified with hydrogen chloride gas (pH=3–4) to give a acidic ethereal solution (no precipitate formed). The solution was concentrated at room temperature to give a yellow solid which was washed with ether to remove most of the orange color. The slightly yellow solid was then recrystallized from acetonitrile at −20° C. The solid was collected and washed with ether to provide (R)-fluoxetine hydrochloride (8) as a white powder (1.90 g, 75%): mp 140°–142° C. (lit.[133b] mp 140°–141.5° C.; $[\alpha]^{23}$D −2.16° (c 1.62, MeOH); (lit.[133b] $[\alpha]^{23}$D −1.97° [c 1.00, MeOH]); $[\alpha]^{23}$D +7.08° (c 1.30, H$_2$O); (lit. $[\alpha]^{23}$D +10.32° [c 1.00, H$_2$O]); IR (KBr, CDCl$_3$ 2950, 2640, 2450, 1620, 1595, 1520, 1360, 1250, 1180, 1170, 1130, 1114, 1070, 840 cm−1; $^1$H NMR (CDCl$_3$) δ9.72 (br, s, 2 H), 7.40–7.43 (d, J=8.7 Hz, 2 H), 7.25–7.33 (m, 5 H), 6.88–6.92 (d, J=8.7 Hz, 2 H), 5.45–5.50 (dd, J=4.6, 7.9 Hz, 1 H), 3.12 (br, s, 2 H), 2.55–2.62 (br, s, 3 H), 2.42–2.52 (m, 2 H); Anal. Calcd. for C$_{17}$H$_{19}$ClF$_3$NO: C, 59.05; H, 5.54; N, 4.05; F, 16.48; Cl, 10.25. Found: C, 58.84; H, 5.55; N, 3.94; F, 16.28; Cl, 10.50.

(S)-Fluoxetine hydrochloride was prepared by the above procedure from (S)-N-methyl-3-phenyl-3-hydroxypropylamine: mp 140°–142° C. (lit[133b] mp 135°–137° C.); $[\alpha]^{23}$D −7.12° (c 1.53, H$_2$O); lit[133b] $[\alpha]^{23}$D −10.85° [c 1.00, H$_2$O]); Anal. Calcd. for C$_{17}$H$_{19}$ClF$_3$NO: C, 59.05; H, 5.54; N, 4.05. Found: C, 59.19; H, 5.42; N, 3.89.

4.2 Example 2

The relative potency and specificity of serotonergic reuptake blockage by optically pure and racemic fluoxetine was studied. The study was carried out to ascertain whether R(−), S(+) and racemic fluoxetine differ in their potency to block serotonin (5HT) uptake into synaptosomes, and to ascertain whether these agents differ in their uptake-inhibiting effects on dopamine (DA) and norepinephrine (NE). The methodology for this study was substantially as follows.

To study high-affinity uptake of $^3$H-monoamines, synaptosomal preparations were made of rat corpus striatum (for DA) and cerebral cortex (for 5HT and NE) using methods published by Kula et al. *Life Sciences*, 34(26) pg. 2567–2575 (1984) and Baldessarini et al., *Life Sciences* 39: pg. 1765–1777, (1986). All tissue were freshly dissected on ice and weighed. Following hand homogenization in 10–35 vols of ice-cold 0.32M sucrose containing nilamide, 34 μM in a Teflon-on-glass homogenizer, tissue was centrifuged for 10 minutes at 900×g, and the resulting supernatant containing synaptosomes was used without further treatment.

Each assay tube contained 50 μl of cerebral homogenate, plus $^3$H-monoamine and test agents (enantiomers, racemate, and standards) in a freshly prepared physiologic buffer solution to provide a final volume of 0.5 ml. Tissue were preincubated for 15 minutes at 37° C. before the assay. Tubes were held on ice until the start of incubation for uptake, which was initiated by adding $^3$H-amine to provide a final concentration of 0.1 μM. Tubes were incubated at 37° C. for 10 minutes with $^3$H-DA (26.0 Ci/mmol), and for 20 minutes with $^3$H-5HT (23.4 Ci/mmol) and $^3$H-NE (11.8 Ci/mmol). The reaction was terminated by immersion in ice and dilution with 3 ml of ice-cold isotonic saline containing 20 mM TRIS buffer (pH 7.0). These solutions were filtered through cellulose ester microfilters, followed by two 3 ml washes of the same buffer. The filter was counted for $^3$H in 3.5 ml of Polyfluor at −50% efficiency for tritium. Blanks (incubated at 0° C., or with specific uptake inhibitors of DA [GBR-12909 10 μM], 5HT [zimelidine 10 μM], or NE [desipramine 10 μM]) were usually indistinguishable for assays without tissue, and averaged 2–3% of total CPM (counts per minute). Results are presented in the following table.

| Fluoxetine Binding Data for Enantiomers - IC$_{50}$ Values (expressed as nM) | | | | | | | |
|---|---|---|---|---|---|---|---|
| Compound | 5-HT1 | 5-HT2 | 5-HT3 | 5-HT uptake | D1 | D2 | DA uptake | NE uptake |
| R-Fluoxetine | >10,000 | 1120 | >1000 | 42.7 | >1000 | >1000 | 4780 | >5000 |
| S-Fluoxetine | >10,000 | 924 | >1000 | 43.0 | >1000 | >1000 | 4910 | >5000 |
| R,S-Fluoxetine | >10,000 | 4100 | >1000 | 45.5 | >1000 | >1000 | 4230 | >5000 |

4.3 Example 3

This study is carried out to ascertain whether R(−), S(+) and racemic fluoxetine differ in their dose-response capacity to affect the pattern and amount of rodent spontaneous and amphetamine evoked locomotor activity and turnover of serotonin and dopamine. The acute effect of the racemic mixture of fluoxetine on serotonin uptake is reflected by a rapid reduction in levels of the intracellular serotonin metabolite 5HIAA (Wong et al., *Drug Devl. Res.* 6: pg. 397–403 (1985)). The racemic mixture of fluoxetine also affects dopamine turnover in striatum. Data from this study provides necessary information on comparable (ED$_{50}$ or ED$_{90}$) doses of the enantiomers of fluoxetine.

The basic methodology for this study is as follows. In one set of experiments, adult male Sprague-Dawley rats (approx 250 g) are injected with either racemic fluoxetine or one of the S(+) or R(−) enantiomers. Approximately 5 animals are tested at each of the following doses: 0, 1, 3, 10, 20, or 30 mg/kg i.p. Injection occurs between 10:00 and 14:00 hours to assess effect on diurnal activity. Ten minutes post-injection, animals are placed in cages on computer-interfaced electronic activity monitors, and the amount and pattern of locomotor activity is quantified in 5 minutes opochs during an hour test period. A second set of animals is pretreated with amphetamines to stimulate motor activity and then subjected to procedures as above.

Immediately following testing, the animals are sacrificed and brains rapidly removed for regional dissection. Tissue sections are removed from frontal cortex, striatum, hippocampus and hypothalamus. Tissue specimens are frozen at −70° C., and will then be assayed for levels of DA, NE, 5HT, DOPAC, HVA, and 5HIAA using High Performance Liquid Chromatography with Electrochemical Detection. Tissue sections are also obtained for measurement of brain levels of fluoxetine, to ascertain whether there are any significant acute pharmacokinetic differences in brain transport.

4.4. Example 4

This study is carried out in order to determine the relative potency and efficacy of optically pure R(−), S(+), and racemic fluoxetine on the self-administration of psychoactive substances.

In these studies, groups of 5–10 rats are trained to self-administer typical psychoactive substances. These psychoactive substances include, but are not limited to, alcohol, opiates (e.g., morphine, fentanyl, heroin), stimulants (e.g., cocaine, amphetamine), caffeine, nicotine, hallucinogens (e.g., LSD), and cannabis. Each group of animals is trained to self-administer one of these substances via a route of administration that includes, but is not limited to, oral, intravenous, subcutaneous, and intracerebroventricular. In some instances, specially-bred rats (e.g., alcohol-preferring rats) are used in these procedures.

Rats are tested to determine if R(−), S(+), or racemic fluoxetine can modify the self-administration of these compounds. Animals either have free access to the psychoactive compound, or the substance is used to reinforce a trained behavior such as lever pressing. Fixed doses of test compound are administered in the range of 0.010 to 30 mg/kg via one of the routes of administration listed above. At the same time, animals are tested for basic locomotor activity such as the amount of lever pressing on a "neutral" lever or ingestion of a non-psychoactive substance (e.g., food or water). The data are analyzed to determine the doses of test compound that can modify self-administration of psychoactive substances without otherwise modifying normal behavior.

4.5 Example 5

This study is carried out in order to determine the duration of action of the R(−), S(+) enantiomers and racemic mixture of fluoxetine following acute administration of these compounds. In particular, this study is to determine the degree and duration of 5HT uptake blockade after acute dose of R(−), S(+) enantiomers and the racemic mixture of fluoxetine, and correlate these observations with brain and plasma levels of the enantiomers and racemic mixture of fluoxetine and nor-fluoxetine.

The methodology of this study is as follows: Adult male Sprague-Dawley rats (approx 250 g) are injected intraperitoneally with comparable (ED$_{90}$—vs 5HIAA) doses of either racemic fluoxetine or one of the enantiomers. At various times (specified below) after fluoxetine administration, the animals are briefly anesthetized using short-acting barbiturate anesthesia, and receive an intracisternal injection of a toxin which is taken into 5HT terminals via the uptake port, and exerts a toxic effect, destroying the nerve terminal and depleting 5HT levels. 5HT uptake inhibitors protect the terminal from such agents by blocking transport into the cell. Animals are sacrificed by decapitation 7 days after this treatment. Blood is collected from the trunk, and hippocampal, striatal and cortical brain regions are rapidly dissected on ice. Tissue samples from one hemisphere are used to assay for residual 5HT concentrations. Tissue samples from the other hemisphere, and plasma samples, are used to determine levels of fluoxetine and its desmethyl metabolite. Drug levels are not measured at every time point, but these samples are collected and frozen at −70° C., so that drug levels can be determined at the most interesting time points (e.g., acute, ¹⁄₂, 2×¹⁄₂). Furthermore, these levels are determined using an assay that is not enantiomer specific.

Time Course for Toxin Administration After i.p. Fluoxetine

| | | |
|---|---|---|
| R(−) | 1, 2, 4, 8, 12, 24 | hr post fluoxetine injection |
| S(+) | 1, 4, 8, 12, 24, 30, 48 | hr post fluoxetine injection |
| RS | 1, 4, 8, 12, 24, 30, 48 | hr post fluoxetine injection |

4.6 Example 6

Oral Formulation

Capsules:

| | Quantity per Capsule (Mg.) | |
|---|---|---|
| Formula | A | B |
| Active ingredient | 10.00 | 20.00 |
| Lactose | 65.75 | 55.75 |
| Corn Starch | 18.75 | 18.75 |
| Magnesium Stearate | 0.50 | 0.50 |
| | 125.00 | 125.00 |

The active ingredient, lactose and corn starch are blended until uniform; then the magnesium stearate is blended into the resulting powder. The resulting mixture is encapsulated into suitably sized two-piece hard gelatin capsules.

4.7 Example 7

Oral Formulation

Tablets:

| | Quantity per Tablet | |
|---|---|---|
| Formula | A | B |
| Active Ingredient | 10.00 | 20.00 |
| Lactose | 62.75 | 52.75 |
| Corn Starch | 3.0 | 3.0 |
| Water (per thousand tablets) | 30.0 ml | 30.0 ml |
| Corn Starch | 18.75 | 18.75 |
| Magnesium Stearate | 0.5 | 0.5 |
| | 125.00 | 125.00 |

*The water evaporates during manufacture

The active ingredient is blended with the lactose until a uniform blend is formed. The smaller quantity of cornstarch is blended with the water to form the resulting corn starch paste. This is then mixed with said uniform blend and mixed until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration.

What is claimed is:

1. A method of eliciting an antidepressant effect in a human which comprises administering to said human in need of antidepressant therapy an effective amount of R(−) fluoxetine, or a pharmaceutically acceptable salt thereof, substantially free of its S(+) stereoisomer.

2. The method of claim 1 wherein the amount administered is about 1 mg to about 100 mg per day.

3. The method according to claim 2 wherein the amount administered is about 5 mg to about 60 mg per day.

4. The method according to claim 1 wherein the amount of R(−) fluoxetine or a pharmaceutically acceptable salt thereof is greater than approximately 99% by weight.

5. The method according to claim 1 wherein R(−) fluoxetine or a pharmaceutically acceptable salt thereof, substantially free of its S(+) stereoisomer is administered together with a pharmaceutically acceptable carrier.

6. A method according to claim 2 or 3 wherein R(−) fluoxetine hydrochloride is administered.

7. A method of suppressing appetite in a human which comprises administering to said human in need of appetite suppression an effective amount of R(−) fluoxetine, or a pharmaceutically acceptable salt thereof, substantially free of its S(+) stereoisomer.

8. The method of claim 7 wherein the amount administered is about 1 mg to about 100 mg per day.

9. The method according to claim 8 wherein the amount administered is about 5 mg to about 60 mg per day.

10. The method according to claim 7 wherein the amount of R(−) fluoxetine or a pharmaceutically acceptable salt thereof is greater than approximately 99% by weight.

11. The method according to claim 7 wherein R(−) fluoxetine or a pharmaceutically acceptable salt thereof, substantially free of its S(+) stereoisomer is administered together with a pharmaceutically acceptable carrier.

12. A method according to claim 8 or 9 wherein R(−) fluoxetine hydrochloride is administered.

13. A method of treating pain in a human comprising administering to said human in need of such treatment an effective amount of R(−) fluoxetine, or a pharmaceutically acceptable salt thereof, substantially free of its S(+) stereoisomer.

14. The method of claim 13 wherein the amount administered is about 1 mg to about 100 mg per day.

15. The method according to claim 14 wherein the amount administered is about 5 mg to about 60 mg per day.

16. The method according to claim 13 wherein the amount of R(−) fluoxetine or a pharmaceutically acceptable salt thereof is greater than approximately 99% by weight.

17. The method according to claim 13 wherein R(−) fluoxetine or a pharmaceutically acceptable salt thereof, substantially free of its S(+) stereoisomer is administered together with a pharmaceutically acceptable carrier.

18. A method according to claim 14 or 15 wherein R(−) fluoxetine hydrochloride is administered.

19. A method of treating at least one psychoactive substance use disorder in a human which comprises administering an effective amount of R(−) fluoxetine, or a pharmaceutically acceptable salt thereof, substantially free of its S(+) stereoisomer.

20. A method of treating at least one obsessive compulsive disorder in a human which comprises administering an effective amount of R(−) fluoxetine, or a pharmaceutically acceptable salt thereof, substantially free of its S(+) stereoisomer.

* * * * *